US009138270B2

(12) United States Patent
Lazoglu et al.

(10) Patent No.: US 9,138,270 B2
(45) Date of Patent: Sep. 22, 2015

(54) BONE PLATE

(71) Applicant: Koc Universitesi, Sariyer, Istanbul (TR)

(72) Inventors: Ismail Lazoglu, Istanbul (TR); Gazi Huri, Ankara (TR); Pinar Huri, Ankara (TR)

(73) Assignee: Koc Universitesi, Istanbul (TR)

( * ) Notice: Subject to any disclaimer, the term of this patent is extended or adjusted under 35 U.S.C. 154(b) by 0 days.

(21) Appl. No.: 14/424,914

(22) PCT Filed: Aug. 28, 2013

(86) PCT No.: PCT/EP2013/067626
§ 371 (c)(1),
(2) Date: Feb. 27, 2015

(87) PCT Pub. No.: WO2014/033088
PCT Pub. Date: Mar. 6, 2014

(65) Prior Publication Data
US 2015/0230838 A1      Aug. 20, 2015

(30) Foreign Application Priority Data

Aug. 28, 2012   (TR) .............................. a 2012/09867

(51) Int. Cl.
*A61B 17/80*        (2006.01)
*A61B 17/58*        (2006.01)
*A61B 17/68*        (2006.01)

(52) U.S. Cl.
CPC ............. *A61B 17/8009* (2013.01); *A61B 17/58* (2013.01); *A61B 17/80* (2013.01); *A61B 17/8004* (2013.01); *A61B 17/8023* (2013.01); *A61B 2017/681* (2013.01)

(58) Field of Classification Search
CPC .. A61B 17/58; A61B 17/68; A61B 2017/681; A61B 17/80; A61B 17/8004; A61B 17/8009; A61B 17/8023

See application file for complete search history.

(56) References Cited

U.S. PATENT DOCUMENTS 3,604,414 A * 9/1971 Borges .......................... 606/105
3,659,595 A * 5/1972 Haboush ........................ 606/71

(Continued)

FOREIGN PATENT DOCUMENTS

FR      1 051 847 A      1/1954
FR      2634368 A1 *     1/1990 ............. A61B 17/58

(Continued)

OTHER PUBLICATIONS

Machine Translation of Massaad (FR 2634368) retrieved from EPO website <http://translationportal.epo.org/emtp/translate/?ACTION=description-retrieval&COUNTRY=FR&ENGINE=google&FORMAT=docdb&KIND=A1&LOCALE=en_EP&NUMBER=2634368&OPS=ops.epo.org/3.1&SRCLANG=fr& TRGLANG=en> on Aug. 6, 2015.*

(Continued)

*Primary Examiner* — Larry E Waggle, Jr.
(74) *Attorney, Agent, or Firm* — Brinks Gilson & Lione

(57) ABSTRACT

An embodiment of a bone plate comprises a main body which is fixed to a side of the fracture and having a hole in which a connecting element is inserted for purposes of this fixation procedure; a movable part which is associated with the main body, is fixed to the other side of the fracture and having a hole in which a connecting element is inserted for purposes of this fixation procedure and being moveable with respect to the main body; a displacement mechanism enabling movement of the movable part relative to the main body, on the center of which it is positioned; a locking element which stops operation of the displacement mechanism, thereby restricting the movement of the movable part; and a displacement element which is associated with the displacement mechanism for controlling thereof externally.

11 Claims, 3 Drawing Sheets

(56) References Cited

U.S. PATENT DOCUMENTS

| | | |
|---|---|---|
| 6,139,316 A | 10/2000 | Sachdeva et al. |
| 2011/0230885 A1 | 9/2011 | Weiner et al. |

FOREIGN PATENT DOCUMENTS

| | | | |
|---|---|---|---|
| WO | WO 02/07620 A2 | 1/2002 | |
| WO | WO 0207620 A2 * | 1/2002 | ............. A61B 17/56 |

OTHER PUBLICATIONS

International Preliminary Report on Patentability with Annexes (Amended Claims), dated Dec. 11, 2014, pp. 1-5, issued in International Application No. PCT/EP2013/067626, issued by International Searching Authority European Patent Office, Berlin, Germany.

International Search Report, dated Nov. 19, 2013, pp. 1-4, issued in International Application No. PCT/EP2013/067626, issued by International Searching Authority European Patent Office, Rijswijk, The Netherlands.

* cited by examiner

BONE PLATE

BACKGROUND

The present disclosure relates to a bone plate suitable for use in surgical bone operations.

In surgical treatment of bone fractures, various means such as intramedullary nails, external fixators and plates may be used. Nowadays, such plates have significant importance in treatment of upper extremity fractures, in particular. The state-of-art bone plates are available in two different designs, locked and unlocked bone plates, and may have varying geometrical forms depending on the shape of the anatomic site they are to be applied to. After having been applied to the bone, these plates do not allow adjusting the fracture line, thus a malpositioning (non-abutment of fracture ends) results in a further procedure to be performed which renders the surgery period 2 or 3 times longer. Accordingly, this situation results in a similar increase in the duration of anesthesia in a patient, and risks of complication (infection, bleeding etc.) as well.

Additionally, the state-of-art bone plates are of static nature, thereby requiring use of auxiliary elements such as external fixators, especially where a bone shortening or bone extension is necessary. This procedure requires a further medical personnel or a second fixation implant, hence causing redundant labor loss, additional cost and needlessly, application of an additional implant to the patient, though temporarily.

BRIEF SUMMARY

The bone plate, suitable for use in surgical operations, comprises at least one main body which is fixed to one side of the fracture and having at least one hole in which at least one connecting element is inserted for purposes of this fixation procedure; at least one movable part which is associated with the main body, is fixed to the other side of the fracture and having at least one hole in which at least one connecting element is inserted for purposes of this fixation procedure, and being moveable relative to the main body; at least one displacement mechanism enabling movement of the movable part relative to the main body, on the center of which it is positioned; at least one locking element which stops operation of the displacement mechanism, thereby limiting the movement of the movable part; and at least one displacement element which is associated with the displacement mechanism for external controlling thereof.

The bone plate is directly fixed to the bone, thus allowing external manipulation. Furthermore, bone segments can be aligned precisely and properly without using inserts introduced into the bone along its axis, and bone plate-bone contact surface is reduced, allowing minimization of the risk of infection. Moreover, non-use of such an insert which is normally introduced into the bone in its full length may prevent vein/nerve injuries that may occur in surgical bone operations.

An aspect of an embodiment is to provide a bone plate which is suitable for surgical bone operations, and at least one part of which is movable.

Another aspect of an embodiment is to provide a bone plate enabling the compression/distraction procedures applied on the bone to be implemented by external manipulation.

Yet another aspect of an embodiment is to provide a bone plate reducing vein/nerve injuries in surgical bone operations to a minimum.

Yet another aspect of an embodiment is to provide a bone plate which reduces bleeding in segmented fractures by means of small incisions in accordance with the procedures of "minimally invasive surgery".

Still another aspect of an embodiment is to provide a bone plate that facilitates the bone extension and shortening operations.

Yet another aspect of an embodiment is to provide a bone plate which has a minimal contact surface with the bone tissue, thereby speeding up union of the fractured bone.

Yet another aspect of an embodiment is to provide a bone plate which is of low injection risk.

Yet another aspect of an embodiment is to provide a bone plate which biomechanically presents a more stable and precise distraction/compression in the fracture line.

Still another aspect of an embodiment is to provide a bone plate suitable for use in fixation of two adjacent bone fractures.

BRIEF DESCRIPTION OF THE DRAWINGS

The exemplary embodiments of the bone plate are illustrated in the enclosed drawings, in which.

Figure 1:
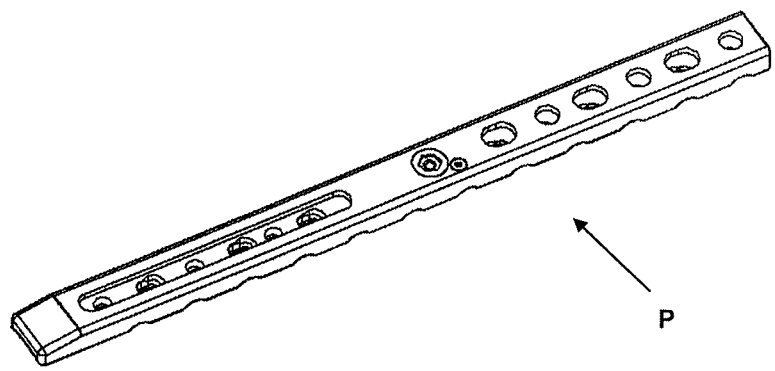
FIG. 1 is a perspective view of a bone plate.

The components shown in the drawings are numbered individually, which numbers correspond to the following:

| Bone plate | (P) |
| Main body | (1) |
| Hole | (1a, 2a) |
| Conduit | (1b, 2b) |
| Seat | (1c) |
| Contact surface | (1d) |
| Movable part | (2) |
| Displacement part | (2c) |
| Gear | (3) |
| Locking element | (4) |
| Displacement element | (5) |

DETAILED DESCRIPTION

In surgical bone operations (for example, in bone fractures, bone extension and shortening operations) various bone plates are used. Particularly, those bone plates used in long bones comprise an insert in the form of a nail which is generally introduced into the bone along its axis. Furthermore, other components are externally fixed to the bone via a plurality of screws and the necessary compression/distraction procedures are performed with these screws and external components. However, introduction of such an insert into the bone in its full length is not only difficult, but also has a greater risk of infection due to the increased contact surface with the bone. Besides, it is very unlikely to apply this procedure in multiple bone fractures and segmented fractures. Additionally, those components and screws which are fastened externally may also cause the patient to suffer from several disturbances during the treatment period. To this end, there is provided an embodiment of a bone plate which is directed to solve the above-mentioned problems.

Figure 2:
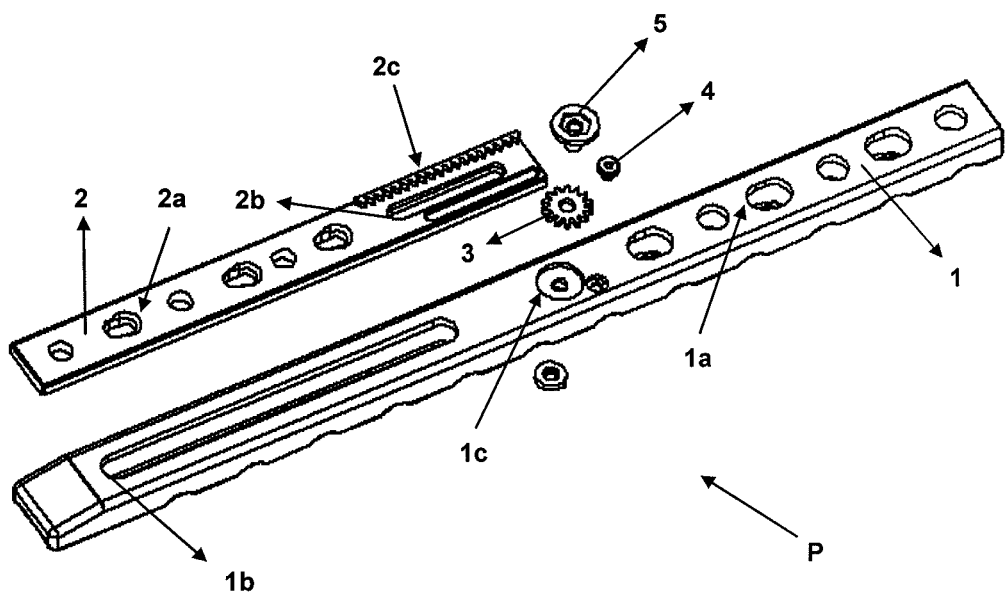
FIG. 2 is a perspective view of the disassembled bone plate.
Figure 3:
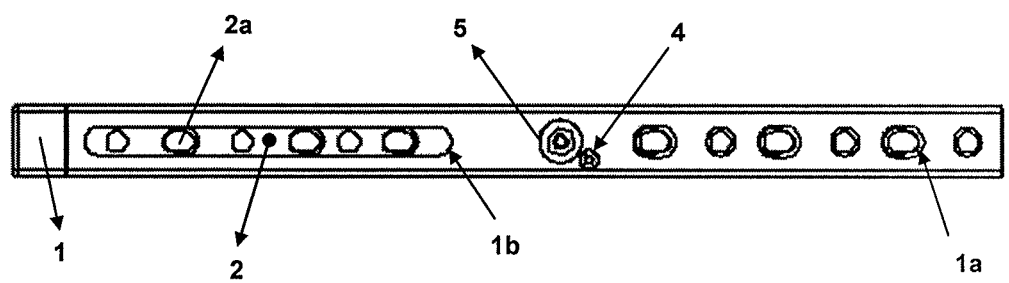
FIG. 3 is a plan view of the bone plate.

The bone plate (P), exemplified in FIGS. 1 and 2, comprises at least one main body (1), at least one movable part (2)

which is associated with the main body (1) (which is preferably positioned on the main body (1) on its side facing to the bone) and is movable relative to the main body (1), and at least one displacement mechanism enabling the movable part (2) to move relative to the main body (1). The main body (1), exemplified in FIGS. 3 and 4, comprises at least one hole (1a) positioned on one side of the main body (1), and in which at least one connecting element (for example, a screw and/or nail) for mounting the said body (1) to one side of the fracture is inserted. The movable part (2), exemplified in FIG. 5, comprises at least one hole (2a) positioned on one side of the movable part (2), and in which at least one connecting element (for example, a screw and/or a nail) for mounting the said part (2) to the other side of the fracture (that is, the side free of the main body (1)) is inserted. The displacement mechanism of the bone plate (P) is positioned on the center of the main body (1), and the displacement plate (P) also comprises at least one locking element (4) which stops operation of the displacement mechanism, thereby limiting the movement of the movable part (2); and at least one displacement element (5) which is associated with the displacement mechanism for controlling thereof externally, as shown in FIG. 2. The said locking element (4) preferably has a screw shape and prevents the movable part (2) from moving, when necessary, by applying a compression pressure thereon.

The bone plate (P) is directly fastened to the bone to be undergone a surgical operation, and preferably the main body (1) of the plate structure is fixed to one side of the fracture via insertion of a connecting element through the hole (1a) located on the main body (1). Preferably, the movable part (2) of the plate structure is similarly fixed to the other side of the fracture via insertion of another connecting element through the hole (2a) located on the movable part (2). Then, during the surgical operation and/or thereafter, the necessary compression/distraction procedures are performed by displacement of the movable part (2) relative to the main body (1) by the displacement mechanism using the displacement element (5). In other words, in bone extension operations, for example, the bone to be extended is separated where appropriate, and the main body (1) and the movable part (2) are mounted to the opposite sides of the fracture. Upon this operation, the movable part (2) is moved to a certain amount and at certain intervals by means of the displacement element (5). This action enables the fractured segments of the bone to move away from each other at a certain distance, in which the movement of the displacement mechanism is restricted by the locking element (4), thereby preventing the displacement mechanism from moving the movable part (2) in an uncontrolled manner. After the bone segments are separated from each other at a certain distance, a certain amount of time is waited to allow re-union of the separated bone segments. Therefore, it is possible to perform bone operations with reduced infection risk and with fewer disturbances to the patient. As another exemplary embodiment, treatment of a fractured bone through a surgical operation allowing union of the bone may be given. In this embodiment, the main body (1) of the bone plate (P) is similarly fixed to one side of the fracture, while the movable part (2) is fixed to the other side thereof. Then, the movable part (2) is made to move by the displacement mechanism using the displacement element (5), and the bone segments are smoothly engaged to each other by approximation and/or separation of the fractured bone segments. When the bone segments engage to each other in a precise and proper manner, the movement of the movable part (2) is restricted by inhibiting the movement of the displacement mechanism via the locking element (4), whereby the said parts are retained stationary in their positions. Thus, bone segments can be aligned precisely and properly without using inserts introduced into the bone along its axis, and bone plate (P)-bone contact surface is reduced, allowing minimization of the risk of infection. Moreover, non-use of such an insert which is normally introduced into the bone in its full length may prevent vein/nerve injuries that may occur in surgical bone operations. Besides, owing to the fact that the displacement mechanism is located on the center of the main body (1), the bone plate (P) displacement mechanism can, as much as possible, be positioned on the center of the fracture, whereby the distraction/compression procedures can be performed in a more stable and precise manner.

Figure 4:
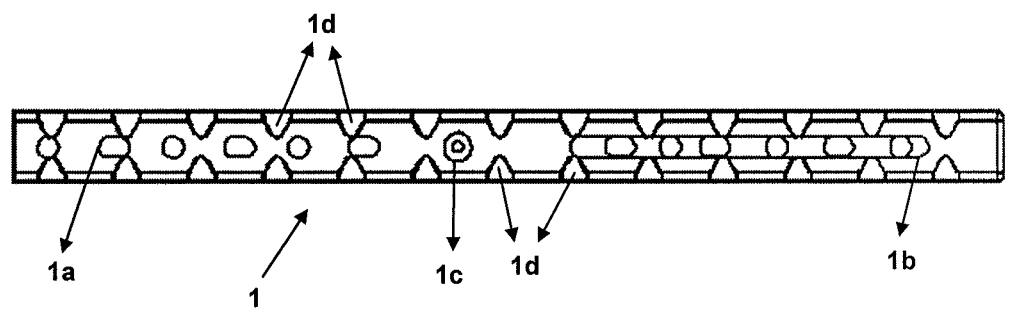
FIG. 4 is a bottom view of the main body which the bone plate includes.
Figure 5:
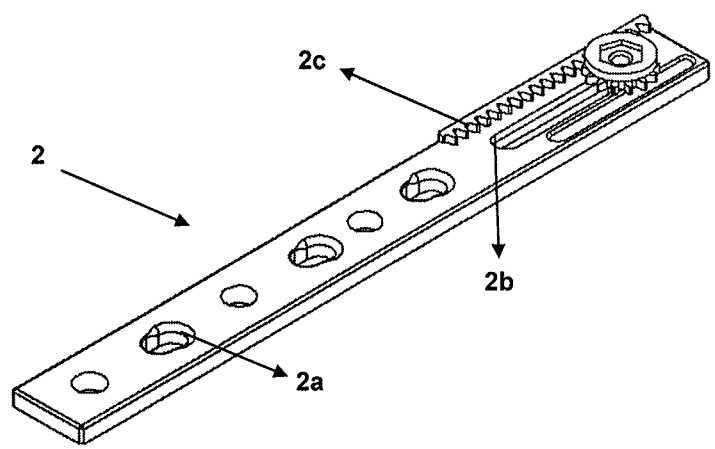
FIG. 5 is a perspective view of the movable part which the bone plate includes.

In a preferred embodiment, shown in FIG. 4, the main body (1) comprises at least two pairs of contact surfaces (1d) in the form of two mutual extensions, which are positioned on the bone contacting side of the main body (1) and form a conduit structure inside the main body (1). Due to these contact surfaces (1d), the movable part (2) is allowed to slide inside the conduit structure formed in the main body (1) without contacting to the bone, and also the bone plate (P)-bone contact surface is reduced. Thus, the risk of infection is minimized and the pone plate (P) is prevented from damaging the bone tissue, veins and/or nerves.

Yet in another exemplary embodiment, shown in FIG. 2, the displacement mechanism includes at least one gear (3) (preferably, a pinion gear) which is positioned on the main body (1) on its side facing to the bone, is associated with the displacement element (5) and, by means of the displacement element (5), can move rotationally, and at least one displacement part (2c) which is positioned on the movable part (2) on its side facing to the main body (1), and transmits the rotational movement of the gear (3) into the linear movement, thus enabling the movable part (2) to move relative to the main body (1). The said displacement part (2c) may preferably have a similar structure to a rack that can be attached to the displacement part (2c) externally, or may be integral with the movable part (2) by making at least one side of the movable part (2), during the manufacturing thereof, in such a structure which transmits the rotational movement of the gear (3) into the linear movement; and the said part (2c) allows sliding movement of the movable part (2). In this embodiment, the locking element (4) is preferably positioned on the main body (1) on its side facing to the bone, and restricts the movement of the movable part (2) by preventing uncontrolled movement of the gear (3). Thus, there is provided a reliable bone plate (P) which is easy to use and implement.

In another exemplary embodiment, the main body (1) comprises at least one conduit (1b) positioned on the other side of the main body (1) and in correspondence with the hole (2a) on the movable part (2). After the main body (1) is fixed to the bone, the connecting element required for fixation of the movable part (2) is passed through this conduit (1b) and inserted into the hole (2a) on the movable part (2), and the connecting element, which fixes the movable part (2) to the bone during the distraction/compression procedures, is allowed to move slidably within said conduit (1b), with the movement of the movable part (2). Thus, a reliable and long-lasting bone plate (P) is obtained through elimination of any frictions and damages that may occur during the movement of the movable part (2), while at the same time excess movement of the movable part (2) during the distraction/compression procedures is prevented by allowing the connecting part (1b) to move within the limits of this conduit (1b), whereby any damages to the bone tissue due to this excess movement is prevented (in other words, the conduit (1b) and the connecting element that moves therein serve as a stopper for the movable part (2)).

Still in a further preferred embodiment, the movable part (2) comprises at least one conduit (2b) positioned on the other side of the movable part (2). In this embodiment, the displacement element (5) is passed though said conduit (2b) and connected to the displacement mechanism. Thus, during the movement of the movable part (2), there is prevented a restriction of the movement of the movable part (2) caused by contact of the same with the displacement element (5), and at the same time since the movable part (2) can move just within the limits of this conduit (2b) excess, uncontrolled movement of the movable part (2) is prevented.

Yet in another exemplary embodiment, the main body (1) comprises at least one seat (1c) positioned on the center of the main body (1), and in which the displacement element (5) is inserted. This seat (1c) bears the displacement element (5), and allows comfortable and harmless control of the movable part (2), which is obtained with enabling easy movement of the displacement element (5) during the distraction/compression procedures.

The bone plate (P) can be used in post-surgical bone operations such as bone extension, which requires external manipulation of the bone, without causing damages and disturbances to the patient while minimizing the risk of infection. Furthermore, thanks to the movable, two-piece structure of the bone plate (P), it is possible to make a bone plate (P) suitable for use in fractures of two adjacent bones with no problems. Additionally, since no inserts to be introduced into the bone along its axis are used, the bone plate (P) can also be used in operations for segmented fractures.

We claim:

1. A bone plate adapted to use in surgical bone operations, which is directly fixed to a bone and allows external manipulation, and comprising; a main body fixed to one side of a fracture and having a hole in which a connecting element is configured to be inserted for purposes of this fixation procedure, wherein the main body comprises at least two pairs of contact surfaces in the form of two mutual extensions, which are positioned on a bone contacting side of the main body and form a conduit structure inside the main body; a movable part which is associated with the main body and allowed to slide inside the conduit structure formed inside the main body without contacting the bone, the movable part being fixed to another side of the fracture and having an other hole in which a connecting element is configured to be inserted for purposes of this fixation procedure; and a displacement mechanism enabling the movable part to slide inside the main body, wherein the displacement mechanism is positioned along a center of the main body and wherein the bone plate comprises: a locking element which restricts sliding of the movable part inside the main body by stopping operation of the displacement mechanism, and a displacement element associated with the displacement mechanism to provide external control thereof; wherein the main body comprises a seat positioned along the center thereof, and in which the displacement element is inserted.

2. The bone plate according to claim 1, wherein the movable part is positioned on the side of said main body that faces the bone.

3. The bone plate according to claim 1, wherein the main body includes a plate structure.

4. The bone plate according to claim 1, wherein the movable part includes a plate structure.

5. The bone plate according to claim 1, wherein said displacement mechanism comprises a gear positioned on the side of the main body that faces the bone, the gear being associated with the displacement element and, by means of the displacement element, being movable rotationally, and a displacement part which is positioned on a side of the movable part that faces the main body, and translates rotational movement of the gear into linear movement, thus enabling the movable part to move relative to the main body.

6. The bone plate according to claim 5, wherein said displacement part is a component that is attached to the movable part externally.

7. The bone plate according to claim 6, wherein the displacement part is a rack.

8. The bone plate according to claim 5, wherein the displacement part is integral with the movable part by making at least one of the side that faces the main body or an other side of the movable part, during manufacturing thereof, in such a structure which translates the rotational movement of the gear into the linear movement.

9. The bone plate according to claim 5, wherein the locking element is located on the side of the main body that faces the bone such that the locking element restricts the movement of the movable part by preventing uncontrolled movement of the gear.

10. The bone plate according to claim 1, wherein the main body comprises a conduit positioned on an other side thereof, and in correspondence with the hole on the movable part.

11. The bone plate according to claim 1, wherein the movable part comprises a conduit positioned on an other side thereof, and through which the displacement element is passed and connected to the displacement mechanism.

* * * * *